(12) United States Patent
Vergez et al.

(10) Patent No.: US 6,676,933 B2
(45) Date of Patent: Jan. 13, 2004

(54) PHARMACEUTICAL COMPOSITION CONTAINING MOSAPRIDE AND PANCREATIN

(75) Inventors: Juan A. Vergez, Buenos Aires (AR); Marcelo A. Ricci, Buenos Aires (AR); Joaquina Faour, Buenos Aires (AR)

(73) Assignee: Osmotica Corp., Tortola (VG)

( * ) Notice: Subject to any disclaimer, the term of this patent is extended or adjusted under 35 U.S.C. 154(b) by 66 days.

(21) Appl. No.: 09/864,767

(22) Filed: May 23, 2001

(65) Prior Publication Data
US 2003/0007962 A1 Jan. 9, 2003

(51) Int. Cl.[7] ..................... A61K 31/74; A61K 38/54; A61K 38/43
(52) U.S. Cl. ................. 424/78.01; 424/94.21; 424/94.1
(58) Field of Search .................. 424/78.01, 94.1, 424/94.21; 514/2

(56) References Cited

FOREIGN PATENT DOCUMENTS

WO     WO 95/01803     1/1995

OTHER PUBLICATIONS

Drug Launches: Product information, Aug. 1999, Zypanar Enzimatico.*
Drug Launches: Product information, Dec. 1996, Gasrimet Enzimat.*
Drug Launches: Product information, Nov. 1995, Pulsar Enzimatico.*
Drug Launches: Product information, Jun. 1994, Sedolax Enzematico.*
Marketletter: Highlights of Astra's Pipeline Presentation; Newsletter Jan. 1998.*
Venturini, J., Ensayo Abierto con la Asociacion Simeticona, Pancreatina, Acido Tioctico y Acidos Biliares, Prensa Med. Argent, 1996, 83 (5): 483–485. (and verified translation thereof).
Maksoud, F. et al., Simethicone Use in Antacid Medications, Manuf. Chem. Aerosol News, 1976, 47 (5): 35–36.
Auld, J. M., Use of Simethicone/Enzyme Agent in Relief of Gastrointestinal Gas, Curr. Ther. Res., 1979, 26 (1): 55–61.
Suramo, I., et al., The Effect of Drugs, Position of the Patient and Filling of the Stomach on Pancreatic Sonography, Ann. Clin. Res. Suppl., 1984, 16 (40): 62–64.

\* cited by examiner

*Primary Examiner*—Christopher R. Tate
*Assistant Examiner*—Patricia Patten
(74) *Attorney, Agent, or Firm*—Rick Matos; Innovar, L.L.C.

(57) ABSTRACT

A pharmaceutical composition contains mosapride, pancreatin and optionally simethicone and is used for treating, preventing or alleviating the symptoms of a gastrointestinal disorder. The pharmaceutical composition is provided in an oral dosage form for administration to a subject.

8 Claims, No Drawings

PHARMACEUTICAL COMPOSITION CONTAINING MOSAPRIDE AND PANCREATIN

FIELD OF THE INVENTION

This invention concerns a pharmaceutical composition comprising mosapride and pancreatin for the treatment of gastrointestinal discomfort. More particularly, the invention pertains to an immediate release solid oral dosage form comprising mosapride, pancreatin and optionally simethicone and to the use of this dosage form for the treatment or prevention of a gastrointestinal disorder or the symptoms associated therewith.

BACKGROUND OF THE INVENTION

Simethicone is used for the relief of discomfort or painful symptoms caused by the presence of excessive gas in the gastrointestinal tract. It is typically recommended for coadministration with an antacid medication, where gas formation is a problem in effective therapy. Simethicone is available in dosage forms including a capsule, suspension, tablet or chewable tablet. Commercial products containing simethicone include Phazyme™, Extra Strength Maalox Anti-Gas™, Flatulex™, Gas-X™, Genasyme™, Maximum Strength Mylanta Gas Relief™, My Baby Gas Relief Drops™, Mylicon™ Drops, Ovol™, and others. Phazyme™ is a combination dosage form containing simethicone and pancreatin. The dose of simethicone required to provide a relief from gastrointestinal pain will vary according to weight and age of a subject receiving the medication. The conventional dose for adults and teenagers for the tablet or capsule ranges from about 60 to 125 mg four times daily after meals and at bedtime. The conventional dose for adults and teenagers for the chewable tablet ranges from about 40 to 125 mg four times daily after meals and at bedtime or the dose may be 150 mg three times daily after meals. Generally, the dose should not exceed 500 mg daily. A tablet containing simethicone, pancreatin, pepsin and belladonna is known.

Pancreatin is an enzymatic preparation made from the pancreatic enzymes of animals. Pancreatin tablets are prescribed for patients who are unable to digest food properly because of an insufficient amount of natural pancreatic excretions. Commercially available products include Solgar™ pancreatin tablets, Twinlab™ pancreatin tablets and others. These tablets generally contain other enzymes such as amylase, protease and lipase as well as a mixture of pharmaceutical excipients.

S. A. Said et al. (*Manuf. Chem. Aerosol News* (1976), 47(5), 35–36) disclose an immediate release coated tablet comprising a core containing simethicone, pepsin, pancreatin and belladonna and a coating surrounding the core and containing pepsin. This tablet is reportedly effective in reducing gastrointestinal gas.

J. M. Auld (*Curr. Ther. Res.* (1979), 26(1), 55–61) discloses an immediate release tablet comprising simethicone and pancreatin. The tablet was administered four times daily to a group of patients over a 2-week period and was reportedly effective at reducing the discomfort and painful symptoms associated with excessive gastrointestinal gas.

I. Suramo et al. (*Ann. Clin. Res., Suppl.* (1984), 16(40), 62–64) disclose an immediate release tablet comprising simethicone and pancreatin. Two tablets were administered four times daily to fifty patients. The tablet was reportedly effective at reducing the amount of gastrointestinal gas.

J. Venturini (*Prensa Med. Argent.* (1996), 83(5), 483–485) discloses an immediate release tablet containing pancreatin, desoxycholic acid, dehydrocholic acid and simethicone, among other things. The tablet was administered twice daily to patients over a period of fourteen days. The tablet was reportedly effective at reducing the gastrointestinal discomfort associated with excessive gas.

Mosapride citrate (mosapride; (+/−)-4-amino-5-chloro-2-ethoxy-N-[[4-(4-fluorobenzyl)-2-morpholinyl]methyl]benzamide citrate; AS-4370; CAS 112885-42-4) is a benzamide-type gastroprokinetic agent that enhances the gastrointestinal motility by stimulating the 5-hydroxytryptamine-4 (5-HT4) receptor. Mosapride citrate is clinically prescribed as a racemate and is metabolized to its des-4-fluorobenzyl structure (M1). The metabolites M1 and M2 of mosapride citrate are generally less efficacious than mosapride.

R. T. Sims et al (International Publication No. WO 95/01803) disclose pharmaceutical compositions comprising an H2 antagonist, such as famotidine, a gastrointestinal motility agent, such as cisapride, and optionally simethicone for the treatment, prevention, or treatment and relief of various mild to moderate symptoms associated with gastrointestinal disorders including indigestion, sour stomach, overindulgence, heartburn, gastroesophageal reflux, constipation, dyspepsia, other gastrointestinal disorders and optionally flatulence.

Thus, the prior art does not disclose a pharmaceutical composition comprising mosapride, pancreatin and optionally simethicone for the treatment, prevention, or treatment and relief of various mild to moderate symptoms associated with gastrointestinal disorders.

SUMMARY OF THE INVENTION

The present invention seeks to overcome at least some of the disadvantages present in the known compositions and to provide a pharmaceutical composition for the treatment of, prevention of, or treatment and relief of various mild to moderate symptoms associated with gastrointestinal disorders including indigestion, sour stomach, overindulgence, heartburn, gastroesophageal reflux, constipation, dyspepsia, other gastrointestinal disorders and optionally flatulence. The pharmaceutical composition comprises mosapride, pancreatin and optionally simethicone or dimethicone. The pharmaceutical composition can be provided in an oral dosage form as disclosed herein. The dosage form can be an immediate release dosage form. The dosage form provides a concurrent, sequential, or combination thereof release of the two and optionally three active agents.

The present invention provides a multi-action approach to the treatment of gastrointestinal disorders in that a gastrointestinal motility agent such as mosapride offers enhanced motility while pancreatin promotes effective digestion and simethicone reduces gastrointestinal gas. The combination simultaneously treats, relieves and/or prevents symptoms associated with excess of gastric acid secretion in the esophagus. Prokinetic agents generally prevent the reflux of gastric acid from the stomach to the esophagus. Conditions or symptoms relieved by the promotion of gastric emptying include but are not limited to gastric stasis, flatulence, dyspepsia, peptic ulcer and reflux esophagitis.

The present invention therefore provides an effective multi-component treatment of gastrointestinal disorders using the combination of pancreatin with the gastrointestinal motility agent mosapride, and optionally with simethicone or dimethicone. The claimed combination is particularly useful for treating gastrointestinal distress.

One aspect of the invention provides a pharmaceutical composition or dosage form consisting essentially of mosapride, simethicone and at least one pharmaceutical excipient. Another aspect of the invention provides a pharmaceutical composition or dosage form consisting essentially of mosapride, simethicone, pancreatin and at least one pharmaceutical excipient. Still another aspect of the invention provides a pharmaceutical composition or dosage form comprising mosapride, simethicone, pancreatin and at least one pharmaceutical excipient.

Specific embodiments of the invention include those wherein: (a) at least one of the mosapride, pancreatin and simethicone or dimethicone is present in a sub-therapeutic amount; (b) wherein no less than 35% of the mosapride is released within 15 minutes and no less than 70% of mosapride is released within 30 minutes after exposure to an aqueous environment; (c) the mosapride, pancreatin and simethicone or dimethicone are released concurrently when the dosage form is placed in an aqueous environment of use; (d) the mosapride and simethicone or dimethicone are released concurrently and the pancreatin is released sequentially, with respect to the mosapride and simethicone or dimethicone, when the dosage form is placed in an aqueous environment of use; (e) the mosapride and simethicone or dimethicone are released into the stomach and the pancreatin is released downstream of the stomach; (f) no less than 80% of the pancreatin is released downstream of the stomach and no more than 10% of the pancreatin is released in the stomach; (g) each of the mosapride, pancreatin and simethicone or dimethicone is present in a therapeutically effective amount; and/or (h) the mosapride is present in an amount of about 2.5–10 mg, the pancreatin is present in an amount of about 100–200 mg, and the simethicone is present in an amount of about 40–1000 mg or the dimethicone is present in an amount of about 20–300 mg.

The dosage forms of the invention are generally solid oral dosage forms. A solid oral dosage form can comprise a core comprising pancreatin and a pharmaceutical excipient, an enteric coat surrounding the core and a drug-containing coat surround the enteric coat and comprising mosapride, a pharmaceutical excipient and simethicone or dimethicone.

Another aspect of the invention provides a method of treating, preventing, or relieving one or more mild to moderate symptoms associated with a gastrointestinal disorder comprising administering the solid dosage form or pharmaceutical composition of the invention. The gastrointestinal disorder is selected from the group consisting of indigestion, sour stomach, overindulgence, heartburn, gastroesophageal reflux, constipation, dyspepsia, and flatulence. The dosage form and pharmaceutical composition can be used to promote gastric emptying, reduce gastrointestinal gas, and promote enzymatic digestion of lipids, proteins and carbohydrate.

Other specific embodiments of the dosage form of the invention are used in biological environments including the oral, gastrointestinal tract, rectal, sublingual, buccal, and other similar environments.

Other features, advantages and embodiments of the invention will become apparent to those of ordinary skill in the art by the following description, accompanying examples and appended claims.

DETAILED DESCRIPTION OF THE INVENTION

The present composition may be administered in an oral dosage form such as tablets, capsules containing granules, and powder for resuspension.

Mosapride, pancreatin, simethicone and dimethicone are available from a number of pharmaceutical companies.

When employed, the amount of simethicone per unit dose may vary depending upon the degree of antiflatulent strength desired, and may range from 40 mg to 1000 mg. Maximum strength antiflatulent is administered in tablet form four times per day may contain 200 mg of simethicone per tablet. Two to four tablets between meals or at bedtime containing the above quantities can be administered daily.

Dimethicone may be used in place of simethicone. When present, dimethicone is administered between in an amount of about 20 mg to 300 mg per unit dose, 2 to 3 times a day.

Mosapride is generally administered in an amount between about 2.5 mg and 10 mg per unit dose, 2 to 4 times a day.

Pancreatin is generally administered in an amount between about 100 mg to 200 mg per unit dose, 3 times a day.

Depending upon the type of oral dosage form used, the dosage form will release the drugs in a concurrent or sequential manner. By "concurrent" is meant that two or more drugs will be released from the dosage form simultaneously for a major period of time in which they are released, however, their respective releases may begin and end at different times. In other words, the dosage form will release the drugs in an overlapping manner (same or different start or finish of their release) but not necessarily in a completely simultaneous manner (same start and finish of their release). By "sequential" is meant that a first one of two or more drugs will begin and end its release before a second one of two or more drugs begins its release.

The dosage form of Example 1 will release no less than 35% of mosapride within 15 minutes and no less than 70% of mosapride within 30 minutes.

The dosage form of Example 2 will release no less than 35% of mosapride within 15 minutes and no less than 70% of mosapride within 30 minutes. No less than 80% of pancreatin dissolves in intestinal medium and no more than 10% of pancreatin dissolves in gastric medium.

The dosage form of Example 3 is a filled hard gelatin capsule consisting essentially of a mixture of two different types of granules. An optional pharmaceutical excipient can be added to the mixture of granules to fill the capsule. The granules of the first group consist essentially of pancreatin and several different pharmaceutical excipients, such as povidone K90 and sodium croscarmellose, that delay the release of the pancreatin such that a none or a only a minor portion of the pancreatin is released into the stomach and all or at least a major portion of the pancreatin is released downstream of the stomach, such as in the ileum, duodenum, jejunum, and/or small intestine, of a subject to which the capsule is administered. The granules of the second group consist essentially of mosapride and simethicone and several different pharmaceutical excipients that to provide a rapid (immediate) release of the mosapride and simethicone into the upper GI tract, especially the stomach. Within the stomach, the mosapride and simethicone are released concurrently. The pancreatin is therefore released sequentially with respect to the mosapride and simethicone.

Example 4 provides a powder for resuspension or reconstitution that consists essentially of mosapride and simethicone. The powder is intended for oral administration as a flavored liquid suspension. The powder can comprise one or more granulations. In Example 4, the powder consists essentially of a first granulation and a second granulation that are mixed together with some pharmaceutical excipients to form a third granulation that is the powder for reconstitution. The first granulation comprises simethicone and pharmaceutical excipients. The second granulation comprises mosapride and pharmaceutical excipients. The third granulation comprises a mixture of the first and second granulations and pharmaceutical excipients. On each occurrence, the pharmaceutical excipients can be the same or different. The powder can be compressed to a form tablet or chewable tablet that is administered to a subject. The powder is generally suspendable or soluble in an aqueous medium. It is generally suspended or dissolved in a beverage, such as milk, water, juice or soda, prior to administration.

The pharmaceutical composition of the invention is advantageous over the above-described dosage forms for treating gastrointestinal disorders. The present composition provides multiple beneficial effects on non-ulcer dyspepsia including promotion of gastric emptying, reduction of gastrointestinal gas, and activation of enzymatic digestion of lipids, proteins and carbohydrates.

The dosage form of the invention can include one or more coats. Those coats are independently selected at each occurrence from an enteric coat, a drug release-controlling coat, and a microporous coat. The tablets of the invention comprise an enteric coat to protect the pancreatin from gastric medium and a finish coat to improve the general product quality, such as aspect, taste, and color. A finish coats that dissolves in more than 10 minutes is generally not used.

Swellable hydrophilic polymers suitable for the pharmaceutical composition include hydrophilic polymers that interact with water and/or aqueous biological fluids, and swell and retain water within their structure. The core, and/or active agent-containing coating preferably expand to about 2 to 50 times of their initial volume. The polymers are of animal, plant or synthetic origin. Hydrophilic polymers suitable for manufacturing the core of the invention preferably include hydroxypropyl methylcelluloses (viscosity from 3 to 100,000 cps, measured in 2% w/v solution); ethylcelluloses (viscosity from 3 to 110 cP, measured in 5% w/v solution); methylcelluloses (viscosity from 10 to 10,000 cP, measured in 2% w/v solution); hydroxypropylcelluloses (general average molecular weight of about 80,000 to 1,150,000) and hydroxyethylcelluloses (viscosity from 2 to 21,000 cP, measured in 2% w/v solution).

Other polymers include (Röhm Pharma, Weiterstadt): Eudragit™ RS 100: solid polymer, Eudragit™ RS 12.5: 12.5% solution in solvent, Eudragit™ RS 30 D: 30% aqueous dispersion and other equivalent products. Eudragit™ RL is readily water permeable while Eudragit™ RS is hardly water permeable. By employing mixtures of both Eudragit™ RL and Eudragit™ RS, membranes having the desired degree of permeability are prepared.

Plasticizers that can be used in the pharmaceutical composition of the invention include all those that are generally incorporated into drug delivery devices. Plasticizers generally improve the mechanical properties and increase the flexibility of the polymeric film. Plasticizers generally reduce cohesive intermolecular forces and increase mobility of polymer chains, thus reducing polymer-polymer interactions. This action is responsible for the changes to the properties of the polymers and films thereof such as a reduction of Tg (glass transition temperature) or softening temperature and the elastic module, increasing polymer flexibility, thus facilitating the process of formation of the membrane or film. A preferred pharmaceutical plasticizer is non-toxic and non-irritating; has a reduced tendency to migrate, extrude or volatilize; and has good miscibility with the polymers in film. Plasticizers that are used in the wall of the present invention include, for example, acetyl triethyl citrate, acetyl tributyl citrate, triethyl citrate, acetylated monoglycerids, glycerol, polyethylene glycol, triacetin, propylene glycol, dibutyl phthalate, diethyl phthalate, isopropyl phthalate, dimethyl phthalate, dactyl phthalate, dibutyl sebacate, dimethyl sebacate, castor oil, glycerol monostearate, fractionated coconut oil, and others. Preferably, polyethylene glycol is used, for example PEG 400, which is available from suppliers such as Aldrich, Sigma Chemical Co. and others.

Suitable plasticizers also include, by way of example and without limitation, low molecular weight polymers, oligomers, copolymers, oils, small organic molecules, low molecular weight polyols having aliphatic hydroxyls, ester-type plasticizers, glycol esters, poly(propylene glycol), multi-block polymers, single-block polymers, low molecular weight poly(ethylene glycol), citrate ester-type plasticizers, triacetin, propylene glycol and glycerin. Such plasticizers can also include ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, acetyltributylcitrate, triethyl citrate, acetyl triethyl citrate, tributyl citrate and allyl glycolate. All such plasticizers are commercially available from sources such as Aldrich or Sigma Chemical Co. A combination of plasticizers may also be used in the present formulation. The PEG based plasticizers are commercially available or can be made by a variety of methods, such as disclosed in Poly(ethylene glycol) Chemistry: Biotechnical and Biomedical Applications (J. M. Harris, Ed.; Plenum Press, NY) the disclosure of which is hereby incorporated by reference.

Materials useful for an external coating include poly(vinylpyrrolidone) (PVP), poly(ethylene glycol) (PEG), hydroxypropyl ethylcellulose, hydroxypropyl methylcellulose, ethylcellulose, hydroxyethylcellulose, dimethylaminoethyl methacrylate-methacrylate acid ester copolymer, combinations thereof and other such materials known by those of ordinary skill in the art. The external layer is dissolved, eroded or completely removed in the environment of use.

Other materials that can be added to the pharmaceutical composition to control the drug-release properties thereof include, for example, high or low molecular weight compounds, organic and inorganic compounds such as salts, acids, bases, chelating agents, sodium chloride, d-mannitol, sucrose, glucose, combinations thereof and other similar or equivalent materials known to those of ordinary skill in the art. Others include potassium chloride, sodium tartrate, glucose, mannitol, sodium acetate, sodium chloride, sodium sulfate, sodium citrate, potassium tartrate, sorbitol, sucrose and combinations thereof.

The tablets of the invention can also comprise an acidifying agent, alkalizing agent, adsorbent, antioxidant, buffering agent, colorant, electrolyte, emulsifying (suspending) agent, flavorant, fragrance, sweetening agent, tablet antiadherent, tablet binder, tablet and capsule diluent, tablet direct compression excipient, tablet disintegrant, tablet glidant, tablet lubricant, tablet or capsule opaquant, vitamin and/or tablet polishing agents.

As used herein, the term "adsorbent" is intended to mean an agent capable of holding other molecules onto its surface by physical or chemical (chemisorption) means. Such compounds include, by way of example and without limitation, powdered and activated charcoal and other such materials known to those of ordinary skill in the art.

As used herein, the term "antioxidant" is intended to mean an agent who inhibits oxidation and is thus used to prevent the deterioration of preparations by the oxidative process. Such compounds include, by way of example and without limitation, ascorbic acid, ascorbic palmitate, Vitamin E, butylated hydroxyanisole, butylated hydroxytoluene, hypophosphorous acid, monothioglycerol, propyl gallate, sodium ascorbate, sodium bisulfite, sodium formaldehyde sulfoxylate, sodium metalbisulfite and other such materials known to those of ordinary skill in the art.

As used herein, the term "alkalizing agent" is intended to mean a compound used to provide alkaline medium for product stability. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, and trolamine and others known to those of ordinary skill in the art.

As used herein, the term "acidifying agent" is intended to mean a compound used to provide an acidic medium for product stability. Such compounds include, by way of example and without limitation, acetic acid, amino acid, citric acid, fumaric acid and other alpha hydroxy acids, such as hydrochloric acid, ascorbic acid, and nitric acid and others known to those of ordinary skill in the art.

As used herein, the term "buffering agent" is intended to mean a compound used to resist a change in pH upon dilution or addition of acid or alkali. Such compounds include, by way of example and without limitation, potassium metaphosphate, potassium phosphate, monobasic sodium acetate and sodium citrate anhydrous and dehydrate and other such materials known to those of ordinary skill in the art.

As used herein, the term "sweetening agent" is intended to mean a compound used to impart sweetness to a preparation. Such compounds include, by way of example and without limitation, aspartame, dextrose, glycerin, mannitol, saccharin sodium, sorbitol, sucrose, fructose and other such materials known to those of ordinary skill in the art.

As used herein, the expression "antiadherent" is intended to mean an agent that prevent the sticking of tablet formulation ingredients to the punches and dies in a tableting machine during production. Such compounds include, by way of example and without limitation, magnesium stearate, calcium stearate, talc, glyceryl behenate, poly(ethylene glycol), hydrogenated vegetable oil, mineral oil, stearic acid, combinations thereof and other such materials known to those of ordinary skill in the art.

As used herein, the term "binder" is intended to mean a substance used to cause adhesion of powder particles in tablet granulations. Such compounds include, by way of example and without limitation, acacia, alginic acid, tragacanth, poly (vinylpyrrolidone), compressible sugar (e.g., NuTab), ethylcellulose, gelatin, liquid glucose, methylcellulose, povidone and pregelatinized starch, combinations thereof and other materials known to those of ordinary skill in the art.

When needed, other binders may also be included in the present pharmaceutical formulation. Exemplary binders include starch, poly(ethylene glycol), guar gum, polysaccharide, bentonites, sugars, invert sugars, poloxamers (PLURONIC™ F68, PLURONIC™ F127), collagen, albumin, celluloses in nonaqueous solvents, combinations thereof and the like. Other binders include, for example, poly(propylene glycol), polyoxyethylene-polypropylene copolymer, polyethylene ester, polyethylene sorbitan ester, poly(ethylene oxide), microcrystalline cellulose, poly (vinylpyrrolidone), combinations thereof and other such materials known to those of ordinary skill in the art.

As used herein, the term "diluent" or "filler" is intended to mean inert substances used as fillers to create the desired bulk, flow properties, and compression characteristics in the preparation of tablets and capsules. Such compounds include, by way of example and without limitation, dibasic calcium phosphate, kaolin, sucrose, mannitol, microcrystalline cellulose, powdered cellulose, precipitated calcium carbonate, sorbitol, starch, combinations thereof and other such materials known to those of ordinary skill in the art.

As used herein, the term "tablet direct compression excipient" is intended to mean a compound used in direct compression tablet formulations. Such compounds include, by way of example and without limitation, dibasic calcium phosphate (e.g. Ditab™), microcrystalline cellulose, direct compression lactose (e.g. Tablettose™, Lactose DT), combinations thereof and other such materials known to those of ordinary skill in the art.

As used herein, the term "glidant" is intended to mean agents used in tablet and capsule formulations to improve flow-properties during tablet compression and to produce an anti caking effect. Such compounds include, by way of example and without limitation, colloidal silica, calcium silicate, magnesium silicate, silicon hydrogel, cornstarch, talc, combinations thereof and other such materials known to those of ordinary skill in the art.

As used herein, the term "lubricant" is intended to mean substances used in tablet formulations to reduce friction during tablet compression. Such compounds include, by way of example and without limitation, calcium stearate, magnesium stearate, mineral oil, stearic acid, zinc stearate, combinations thereof and other such materials known to those of ordinary skill in the art.

As used herein, the term "tablet opaquant" is intended to mean a compound used to used in tablet coatings or capsules providing useful opacity which can aid the stability to the light in case of sensitive agents. It may be used alone or in combination with a colorant. Such compounds include, by way of example and without limitation, titanium dioxide and other such materials known to those of ordinary skill in the art.

As used herein, the term "tablet polishing agent" is intended to mean a compound used to impart brightness to the surface of the coated tablets. Such compounds include, by way of example and without limitation, carnauba wax, white wax, combinations thereof and other such materials known to those of ordinary skill in the art.

As used herein, the term "tablet disintegrant" or "superdisintegrant" is intended to mean a compound used in solid dosage forms to promote the disruption of the solid mass into smaller particles which are more readily disiiersed or dissolved. Exemplary disintegrants include, by way of example and without limitation, starches such as corn starch, potato starch, pre-gelatinized and modified starches thereof, cross-linked PVP, sweeteners, clays, such as bentonite, microcrystalline cellulose (e.g. Avicel™), carboxymethylcellulose calcium, cellulose polyacrylin potassium (e.g. Amberlite™), alginates, sodium starch glycolate, gums such as agar, guar, locust bean, karaya, pectin, tragacanth, combinations thereof and other such materials known to those of ordinary skill in the art.

Electrolytes include calcium gluconate, calcium lactate, potassium chloride, potassium sulfate, sodium chloride, sodium fluoride, ferrous lactate, ferrous gluconate, ferrous sulfate, ferrous fumarate, sodium lactate, dicalcium phosphate, sodium benzoate, and sodium acetate.

As used herein, the term "colorant" is intended to mean a compound used to impart color to pharmaceutical preparations. Such compounds include, by way of example and without limitation, FD&C Red No. 3, FD&C Red No. 20, FD&C Yellow No. 6, FD&C Blue No. 2, D&C Green No. 5, D&C Orange No. 5, D&C Red No. 8, caramel, and iron oxide (black, red, yellow), other F.D. & C. dyes and natural coloring agents such as grape skin extract, beet red powder, beta-carotene, annato, carmine, turmeric, paprika, combinations thereof and other such materials known to those of ordinary skill in the art.

As used herein, the term "flavorant" is intended to mean a compound used to impart a pleasant flavor and often odor to a pharmaceutical preparation. Exemplary flavoring agents or flavorants include synthetic flavor oils and flavoring aromatics and/or natural oils, extracts from plants, leaves, flowers, fruits and so forth and combinations thereof. These may also include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Other useful flavors include vanilla, citrus oil, including lemon, orange, grape, lime and grapefruit, and fruit essences, including apple, pear, peach, strawberry, raspberry, cherry, plum, pineapple, apricot and so forth. Flavors, which have been found to be particularly useful, include commercially available orange, grape, cherry and bubble gum flavors and mixtures thereof. The amount of flavoring may depend on a number of factors, including the desired organoleptic effect. Flavors will be present in any amount as desired by the artisan of ordinary skill in the art. Particularly preferred flavors are the grape and cherry flavors and citrus flavors such as orange.

Acceptable emulsifying or suspending agents such as PVP, gelatin, natural sugars, corn sweeteners, natural and synthetic gums such as acacia, guar gum, agar, bentonite, carboxymethylcellulose sodium, polyethylene glycol and waxes, may also be admixed with the active components.

The pharmaceutical formulation of the invention can also include oils such as fixed oils, peanut oil, sesame oil, cottonseed oil, corn oil and olive oil; fatty acids such as oleic acid, stearic acid and isostearic acid; and fatty acid esters such as ethyl oleate, isopropyl myristate, fatty acid glycerides and acetylated fatty acid glycerides. The device can also include alcohol such as ethanol, isopropanol, hexadecyl alcohol, glycerol and propylene glycol; glycerol ketals such as 2,2-dimethyl-1,3-dioxolane-4-methanol; ethers such as poly (ethyleneglycol) 450; petroleum hydrocarbons such as mineral oil and petrolatum; water; mixtures thereof; or a pharmaceutically suitable surfactant, suspending agent or emulsifying agent.

Soaps and synthetic detergents may be employed as surfactants and as vehicles for detergent compositions. Suitable soaps include fatty acid alkali metal, ammonium, and triethanolamine salts. Suitable detergents include cationic detergents such as dimethyl dialkyl ammonium halides, alkyl pyridinium halides, and alkylamine acetates; anionic detergents such as alkyl, aryl and olefin sulfonates, alkyl, olefin, ether and monoglyceride sulfates, and sulfosuccinates; non-ionic detergents such as fatty amine oxides, fatty acid alkanolamides, and poly(oxyethylene)-block-poly (oxypropylene) copolymers; amphoteric detergents such as alkyl β-aminopropionates and 2-alkylimidazoline quaternary ammonium salts; and mixtures thereof.

Various other components, not otherwise listed above, can be added to the present formulation to provide a desired release profile. Such components include, by way of example and without limitation, glycerylmonostearate, nylon, cellulose acetate butyrate, d,l-poly (lactic acid), 1,6-hexanediamine, diethylenetriamine, starches, derivatized starches, acetylated monoglycerides, gelatin coacervates, poly(styrene-maleic acid) copolymer, glycowax, castor wax, stearyl alcohol, glycerol palmitostearate, poly ethylene, poly (vinyl acetate), poly(vinyl chloride), 1,3-butylene-glycoldimethacrylate, ethyleneglycol-dimethacrylate and methacrylate hydrogels.

It should be understood that the compounds used in the art of pharmaceutical formulation generally serve a variety of functions or purposes. Thus, if a compound named herein is mentioned only once or is used to define more than one term herein, its purpose or function should not be construed as being limited solely to that named purpose(s) or function(s).

Since combinations of drugs are administered for the treatment of gastrointestinal disorders, the pharmaceutical composition of the invention can further include cisapride, domperidone, or metoclopramide.

Nutritional agents including ascorbic acid, niacin, nicotinamide, folic acid, choline biotin, panthothenic acid, vitamins, essential amino acids, and essential fats can also be added. As used in this disclosure, the term vitamin refers to trace organic substances that are required in the diet. For the purposes of the present invention, the term vitamin(s) include, without limitation, thiamin, riboflavin, nicotinic acid, pantothenic acid, pyridoxine, biotin, folic acid, vitamin B12, lipoic acid, ascorbic acid, vitamin A, vitamin D, vitamin B and vitamin K. Also included within the term vitamin are the coenzymes thereof. Coenzymes are specific chemical forms of vitamins and can include thiamin pyrophosphates (TPP), flavin mononucleotide (FMN), and flavin adenine dinucleotide (FAD). Nicotinamide adenine dinucleotide (NAD), Nicotinamide adenine dinucleotide phosphate (NADP), Coenzyme A (CoA), pyridoxal phosphate, biocytin, tetrahydrofolic acid, coenzyme B12, lipolysine, 11-cis-retinal, and 1,25-dihydroxycholecalciferol. The term vitamin(s) also includes choline, carnitine, and alpha, beta, and gamma carotene.

The above-mentioned lists should not be considered exhaustive and are merely exemplary of the many embodiments considered within the scope of the invention. Many other active compounds can be administered with the formulation of the present invention.

The active agent can be present in its neutral, ionic, salt, basic, acidic, natural, synthetic, diastereometric, isomeric, enantiomerically pure, racemic, hydrate, chelate, derivative, analog, or other common form. The therapeutic compound (s) contained within the present device can be formulated as its pharmaceutically acceptable salts. As used herein, "pharmaceutically acceptable salts" refers to derivatives of the disclosed compounds wherein the therapeutic compound is modified by reacting it with an acid or base as needed to form an ionically bound pair. Examples of pharmaceutically acceptable salts include conventional non-toxic salts or the quaternary ammonium salts of the parent compound formed, for example, from non-toxic inorganic or organic acids. Suitable non-toxic salts for basic active agents include those derived from inorganic acids such as hydrochloric, hydrobromic, sulfuric, sulfonic, sulfamic, phosphoric, nitric and others known to those of ordinary skill in the art. The salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and others known to those of ordinary skill in the art. Suitable non-toxic salts for acidic active agents include those derived from an organic amine, an alkali metal hydroxide, an alkali metal alkoxide, a primary amine, a secondary amine, a tertiary amine, a quaternary amine, an aromatic amine, a heterocyclic amine, or an inorganic base. The pharmaceutically acceptable salts of the present invention can be synthesized from the parent therapeutic compound which contains a basic or acidic moiety by conventional chemical methods. Lists of other suitable salts are found in *Remington's Pharmaceutical Sciences*, 17$^{th}$. ed., Mack Publishing Company, Easton, Pa., 1985, p. 1418, the relevant disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with tissues of human beings and animals and without excessive toxicity, irritation, allergic response, or any other problem or complication, commensurate with a reasonable benefit/risk ratio.

The amount of compound ncorporated in each dosage form of the invention will be selected according to known principles of pharmacy. A therapeutically effective amount or sub-therapeutic amount of compound is specifically contemplated. The term "therapeutically effective amount" means the amount or quantity of a drug or pharmaceutically active substance which is enough to provide a desired therapeutic response alone, or in other words, the amount which is sufficient to elicit an appreciable biological response when administered alone, absent another therapeutic agent. The appreciable biological response may occur as a result of administration of single or multiple unit doses of an active substance. Depending upon the active substance used and upon the amount of active substance present in a particular dosage form according to the invention, a unit dose may comprise one or more such dosage forms. A sub-therapeutic amount is an amount less than that amount generally recognized as the therapeutically effective amount.

The active agents in the pharmaceutical composition of the invention provide at least an additive therapeutic effect. An additive therapeutic benefit occurs when each drug is provided at its therapeutically effective dose and the drugs together provide a cumulative therapeutic benefit. This occurs when each drug provides its respective therapeutic benefit approximating the benefit provided when the drug is administered alone.

If desired, the dosage form of the invention can be coated with a finish coating as is commonly done in the art to provide the desired shine, color, taste or other aesthetic characteristics. Materials suitable for preparing the finish coating are well known to those of ordinary skill in the art.

The pharmaceutical composition of the invention, and a dosage form containing it, is used to treat a gastrointestinal disorder. The invention provides a method of treating, preventing or alleviating a mild to moderate symptom associated with a gastrointestinal disorder. The method of treating comprises the step of administering to a subject suffering a gastrointestinal disorder an effective amount of the pharmaceutical composition thereby ameliorating or reducing the severity of the disorder. The composition will be administered for a period of time sufficient to provide its therapeutic benefit. Alternatively, a sufficient number of unit doses of a dosage form containing the pharmaceutical composition will be administered to provide its therapeutic benefit.

The method of preventing comprises the step of administering to a subject prone to suffering a gastrointestinal disorder an effective amount of the pharmaceutical composition thereby preventing the occurrence of the disorder in the subject or thereby delaying the occurrence of the disorder in the subject a period of time greater than the subject generally experiences between bouts of the disorder when the subject is not being administered the pharmaceutical composition.

The method of alleviating one or more symptoms associated with a gastrointestinal disorder comprises the step of administering to a subject suffering a gastrointestinal disorder an effective amount of the pharmaceutical composition thereby eliminating or reducing the severity of one or more disorders typically associated with that gastrointestinal disorder. The composition will be administered for a period of time sufficient to provide its therapeutic benefit. Alternatively, a sufficient number of unit doses of a dosage form containing the pharmaceutical composition will be administered to provide its therapeutic benefit.

The following examples should not be considered exhaustive, but merely illustrative of only a few of the many embodiments contemplated by the present invention. The methods described herein can be followed to prepare dosage forms according to the invention.

EXAMPLE 1

Rapid Release Tablet Consisting Essentially of Mosapride and Simethicone

The following table includes a list of ingredients and the approximate amounts in which they are present in the above-identified tablets.

| Ingredient | Amount (mg) |
| --- | --- |
| Simethicone | 220.00 |
| Mosapride citrate (dehydrated) | 5.28 |
| Microcrystalline cellulose | 208.34 |
| Gelatin | 70.00 |
| Yellow Lake FD&C N°10 | 1.00 |
| Magnesium stearate | 1.00 |
| Pregelatinized starch | 10.00 |
| Yellow Lake FD&C N° 6 | 0.50 |
| Colloidal silicon dioxide | 4.00 |
| Poloxamer 188 | 0.09 |
| Povidone (PVP K30) | 8.00 |
| Purified water (before drying) | 2.00 (ml) |

The above tablets are made as follows. Microcrystalline cellulose and 50% of the total quantity of pregelatinized starch are thoroughly mixed. Simethicone is then blended in with a high shear mixer to form a first blend. A granulating solution is prepared by heating purified water and adding in gelatin, and colorants to the water with continuous stirring. The first blend is granulated with the granulating solution to form a first granulate. This granulate is then dried.

Poloxamer 188 is dissolved in purified water and the total quantity of mosapride citrate (dihydrate) is added with stirring until complete dissolution. The Poloxamer/mosapride solution is added to the first granulate with mixing. The final wet granulate is dried in a fluid bed dryer and sieved through a USP No. 12 Mesh screen. The remaining 50% of the pregelatinized starch, the colloidal silicon dioxide and the magnesium stearate are blended with the granulate for five minutes and the entire mixture is pressed into tablets.

EXAMPLE 2

Rapid Release Tablets Consisting Essentially of Mosapride, Simethicone and Pancreatin The following table includes a list of ingredients and the approximate amounts in which they are present in the above-identified tablets.

| Ingredient | Amount (mg) |
| --- | --- |
| Simethicone | 220.00 |
| Pancreatin 6NF | 153.00 |
| Mosapride citrate (dehydrated) | 5.28 |
| Lactose monohydrate | 292.80 |
| Sodium croscarmellose | 58.40 |
| Polysorbate 20 | 8.00 |
| Povidone (PVP K90) | 4.80 |
| Gelatin | 70.00 |
| Microcrystalline cellulose | 210.52 |
| Talc | 2.00 |
| Yellow Lake N°10 D&C | 1.00 |
| Magnesium stearate | 1.00 |
| Pregelatinized starch | 22.00 |
| Yellow Lake FD&C N° 6 | 0.50 |
| Colloidal silicon dioxide | 20.00 |
| Blue FD&C N°1 | 2.00 |
| Menthol | 1.50 |
| Cellulose Acetophthalate | 15.00 |
| Poloxamer 188 | 0.09 |
| Povidone (PVP K30) | 32.83 |
| Polyethylene glycol 4000 | 0.75 |
| Purified Water (before drying) | 2.00 (ml) |

The above tablets were made as follows. The actual amounts used varied according to the batch size as the amounts relative to one another were kept approximately constant. Pancreatin NF, Povidone K90 and sodium croscarmellose were weighed and placed in a mixer. These ingredients were granulated with 96° ethanol. The granulate was sieved through a USP 12 mesh and blended with magnesium stearate and talc. The blend was compressed into tablet cores, which were then coated with a composition containing cellulose acetophthalate and PEG 4000. This coat serves as an enteric coat that protects the pancreatin from the gastric medium. The pancreatin will generally dissolve in the intestinal medium.

A second composition for compressing around the coated cores was prepared by thoroughly mixing microcrystalline cellulose and 50% of the pregelatimzed starch in a mixer. Simethicone was added to the mixture in a high shear mixer. A binder composition was prepared by heating purified water and adding gelatin, and the colorants to it while stirring. The binder composition was used to granulate the solid mixture of MCC, simethicone and pregelatinized starch. Poloxamer 188 was dissolved in purified water and the mosapride citrate dihydrate was added to it and stirred until completely dissolved. This solution was added to the granulate which was dried in a fluid bed dryer and sieved through a USP No. 12 mesh screen. The remaining 50% of the pregelatinized starch, the colloidal silicon dioxide, menthol, and magnesium stearate were blended with this second granulate. This second composition was then compressed onto the coated tablet core.

In this embodiment, the pancreatin is release in the gut; therefore it is released after the mosapride and simethicone. Although the release of pancreatin is intended to be sequential, with respect to mosapride and simethicone, some slight overlap in their deliveries may occur.

EXAMPLE 3

Hard Gelatin Capsules Consisting Essentially of Mosapride, Simethicone and Pancreatin The following table includes a list of ingredients and the approximate amounts in which they are present in the above-identified capsules.

| Ingredient | Amount (mg) per capsule |
| --- | --- |
| Simethicone | 220.00 |
| Pancreatin 6NF | 153.00 |
| Mosapride Citrate Dehydrated | 5.28 |
| Lactose Monohydrate | 292.80 |
| Sodium Croscarmellose | 58.40 |
| Polysorbate 20 | 8.00 |
| Povidona (PVP K90) | 4.80 |
| Gelatin | 70.00 |
| Cellulose microcrystalline | 210.52 |
| Talc | 2.00 |
| Yellow Lake N°10 D&C | 1.00 |
| Magnesium Stearate | 1.00 |
| Pregelatinized starch | 22.00 |
| Yellow Lake N° 6 D&C | 0.50 |
| Colloidal Silicon Dioxide | 20.00 |
| Blue FDYC N°1 | 2.00 |
| Menthol | 1.50 |
| Cellulose Acetopthalate | 15.00 |
| Poloxamer 188 | 0.09 |
| Povidone (PVP K30) | 32.83 |
| Polyethylene Glycol 4000 | 0.75 |
| Purified Water | 2.00 (ml) |

The above capsules are made as follows. A first composition is prepared by thoroughly mixing Pancreatin NF, povidone K90 and sodium croscarmellose in a mixer. These ingredients are granulated with 96° ethanol. The granulate is sieved through a USP 12 mesh and dried in a fluid bed dryer. The granules are then coated with a composition containing cellulose acetophthalate and PEG 4000. No less than 80% of pancreatin dissolves in intestinal medium and no more than 10% of pancreatin dissolves in gastric medium.

A second composition is prepared by thoroughly mixing microcrystalline cellulose, and 50% of the pregelatinized starch in a mixer. Simethicone is added to the mixture in a high shear mixer. A binder composition is prepared by heating purified water and adding gelatin, and the colorants to it while stirring. The binder composition is used to granulate the solid mixture of MCC, simethicone, and pregelatinized starch. Poloxamer 188 are dissolved in purified water and the mosapride citrate dihydrate is added to it and stirred until completely dissolved. This solution is added to the granules that are dried in a fluid bed dryer and sieved through a USP 12 mesh screen. The first and second compositions are then mixed. This final granulated composition is used to fill hard gelatin capsules. No less than 35% of mosapride dissolves within 15 minutes and no less than 70% of mosapride dissolves within 30 minutes.

EXAMPLE 4

Dry Granulation of Mosapride and Simethicone for Resuspension

The following table includes a list of ingredients and the amounts in which they are present in the above-identified dry granulation.

| Ingredient | Amount (mg) per 2 ml dose. |
|---|---|
| Simethicone | 220.00 |
| Mosapride Citrate Dehydrated | 5.28 |
| Mannitol | 249.20 |
| Polysorbate 80 | 16.66 |
| Poloxamer 188 | 3.40 |
| Maltodextrin | 400.00 |
| Colloidal silicon dioxide | 80.00 |
| Methylparaben | 3.60 |
| Propylparaben | 0.40 |
| Flavor (banana flavored powder) | 4.00 |
| Sodium Cyclamate | 14.00 |
| Sodium saccharin | 1.20 |
| Mint flavor powder | 2.00 |

The dry granulation for resuspension is manufactured as follows. A first composition is prepared by thoroughly mixing simethicone, maltodextrin and colloidal silicon dioxide in a high shear mixer. Polysorbate 80 is added to the mixture that is then sieved through a USP 10 mesh sieve. A second composition is prepared dissolving poloxamer 188 in 96° ethanol, adding dehydrated mosapride citrate to it and stirring until complete dissolution. This solution is used to granulate the mannitol that is then tray dried at 30° C. for 10 minutes. These dried granules are passed through a 16 mesh screen to obtain a consistency in granule size. Both granulated compositions are mixed and blended with methlparaben, propylparaben, mint flavor, sodium saccharin and sodium cyclamate. The final granulated composition is weight packed into bottles.

The above is a detailed description of particular embodiments of the invention. It is recognized that departures from the disclosed embodiments may be made within the scope of the invention and that obvious modifications will occur to a person skilled in the art. Those of skill in the art should, in light of the present disclosure, appreciate that many changes can be made in the specific embodiments which are disclosed herein and still obtain a like or similar result without departing from the spirit and scope of the invention. All of the embodiments disclosed and claimed herein can be made and executed without undue experimentation in light of the present disclosure.

We claim the following:

1. A solid oral dosage form comprising:
   a) a core comprising pancreatin and a pharmaceutical excipient;
   b) an enteric coat surrounding the core; and
   c) a drug-containing coat surrounding the enteric coat and comprising mosapride, a pharmaceutical excipient and simethicone or dimethicone.

2. The dosage form of claim 1, wherein no less than 35% of the mosapride is released within 15 minutes and no less than 70% of the mosapride is released within 30 minutes after exposure to an aqueous environment of use.

3. The dosage form of claim 1, wherein the mosapride, pancreatin and simethicone or dimethicone are released concurrently when the dosage form is placed in an aqueous environment of use.

4. The dosage form of claim 1, wherein the mosapride and simethicone or dimethicone are released concurrently and the pancreatin is released sequentially, with respect to the mosapride and simethicone or dimethicone, when the dosage form is placed in an aqueous environment of use.

5. The dosage form of claim 4, wherein the mosapride and simethicone or dimethicone are released into the stomach and the pancreatin is released downstream of the stomach when administered to a subject.

6. The dosage form of claim 5, wherein no less than 80% of the pancreatin is released downstream of the stomach and no more than 10% of the pancreatin is released in the stomach when administered to a subject.

7. The dosage form of claim 6, wherein the mosapride and simethicone or dimethicone are released into the stomach and the pancreatin is released downstream of the stomach when the dosage form is administered to a subject.

8. The dosage form of claim 1, wherein the mosapride is present in an amount of about 2.5–10 mg, the pancreatin is present in an amount of about 100–200 mg, and the simethicone is present in an amount of about 40–1000 mg or the dimethicone is present in an amount of about 20–300 mg.

* * * * *